(12) United States Patent
Siniaguine

(10) Patent No.: US 8,237,007 B2
(45) Date of Patent: Aug. 7, 2012

(54) WOUND DRESSING WITH CONTROLLABLE PERMEABILITY

(75) Inventor: Oleg Siniaguine, San Carlos, CA (US)

(73) Assignee: PolyRemedy, Inc., San Jose, CA (US)

( * ) Notice: Subject to any disclaimer, the term of this patent is extended or adjusted under 35 U.S.C. 154(b) by 971 days.

(21) Appl. No.: 11/972,452

(22) Filed: Jan. 10, 2008

(65) Prior Publication Data

US 2008/0167594 A1  Jul. 10, 2008

Related U.S. Application Data

(60) Provisional application No. 60/884,321, filed on Jan. 10, 2007, provisional application No. 60/888,693, filed on Feb. 7, 2007.

(51) Int. Cl.
*A61F 13/00* (2006.01)

(52) U.S. Cl. .............................. 602/41; 602/42; 602/48

(58) Field of Classification Search .............. 602/41–59; 424/443–449; 604/304–308
See application file for complete search history.

(56) References Cited

U.S. PATENT DOCUMENTS

| | | | |
|---|---|---|---|
| 2,682,873 A | 7/1954 | Idnis | |
| 2,836,178 A * | 5/1958 | Barr | 602/59 |
| 3,140,572 A | 7/1964 | Petersen et al. | |
| 3,425,412 A * | 2/1969 | Pope | 602/59 |
| 3,729,892 A | 5/1973 | Aslund et al. | |
| 3,811,445 A | 5/1974 | Dostal | |
| 4,347,841 A | 9/1982 | Benyo et al. | |
| 4,522,203 A | 6/1985 | Mays | |
| 4,630,426 A | 12/1986 | Gentry | |
| 4,751,133 A | 6/1988 | Szycher et al. | |
| 4,869,936 A | 9/1989 | Moskowitz et al. | |
| 4,917,688 A | 4/1990 | Nelson et al. | |
| 4,948,540 A | 8/1990 | Nigam | |
| 4,957,795 A | 9/1990 | Riedel | |
| 5,000,172 A | 3/1991 | Ward | |
| 5,265,605 A | 11/1993 | Afflerbach | |
| 5,340,363 A | 8/1994 | Fabo | |
| 5,395,305 A | 3/1995 | Koide et al. | |
| 5,489,437 A | 2/1996 | Marra | |
| 5,520,735 A | 5/1996 | Mulder | |
| 5,520,762 A | 5/1996 | Rasmussen et al. | |

(Continued)

FOREIGN PATENT DOCUMENTS

EP  0509703 B1  10/1992

(Continued)

OTHER PUBLICATIONS

Lowe, U.S. Appl. No. 60/840,412, filed Aug. 28, 2006.*

(Continued)

*Primary Examiner* — Kim M Lewis
(74) *Attorney, Agent, or Firm* — Fenwick & West LLP

(57) ABSTRACT

Wound dressings and methods of manufacturing wound dressings are provided. The wound dressings include portions that are converted from a moisture vapor permeable material to a material having reduced moisture vapor permeability. The conversion may be accomplished in a variety of ways. In some embodiments, a solvent is used to dissolve a porous material to thereby form a non-porous film. In other embodiments, heat is applied to melt a porous material to thereby form a non-porous film. The heat may be applied using a heated gas or a heating element to directly or indirectly heat the material.

15 Claims, 9 Drawing Sheets

U.S. PATENT DOCUMENTS

| | | | |
|---|---|---|---|
| 5,588,428 A | 12/1996 | Smith et al. | |
| 5,641,501 A | 6/1997 | Cooper et al. | |
| 5,653,699 A | 8/1997 | Reed et al. | |
| 5,681,579 A | 10/1997 | Freeman | |
| 5,741,509 A | 4/1998 | Kushner | |
| 5,757,498 A | 5/1998 | Klein, II et al. | |
| 5,762,620 A | 6/1998 | Cartmell et al. | |
| 5,785,697 A | 7/1998 | Trombetta et al. | |
| 5,891,078 A | 4/1999 | Turngren et al. | |
| 5,899,871 A | 5/1999 | Cartmell et al. | |
| 5,935,363 A | 8/1999 | Gilman et al. | |
| 6,004,253 A | 12/1999 | Riedel et al. | |
| 6,043,408 A * | 3/2000 | Geng | 602/58 |
| 6,051,747 A | 4/2000 | Lindqvist et al. | |
| 6,062,285 A | 5/2000 | Dotta et al. | |
| 6,071,267 A | 6/2000 | Zamierowski | |
| 6,153,215 A | 11/2000 | Samuelsen et al. | |
| 6,245,960 B1 | 6/2001 | Eaton | |
| 6,284,941 B1 | 9/2001 | Cox et al. | |
| 6,297,420 B1 | 10/2001 | Heincke | |
| 6,313,369 B1 | 11/2001 | Schiraldi et al. | |
| 6,420,622 B1 | 7/2002 | Johnston et al. | |
| 6,512,160 B1 | 1/2003 | Rutsky | |
| 6,520,425 B1 | 2/2003 | Reneker | |
| 6,655,112 B1 | 12/2003 | Cremer et al. | |
| 6,662,051 B1 | 12/2003 | Eraker et al. | |
| 6,753,454 B1 | 6/2004 | Mello et al. | |
| 6,765,123 B2 | 7/2004 | de Jong et al. | |
| 6,787,682 B2 * | 9/2004 | Gilman | 602/58 |
| 6,967,261 B1 | 11/2005 | Soerens et al. | |
| 7,105,058 B1 | 9/2006 | Sinyagin | |
| 7,347,846 B2 | 3/2008 | Hermansson et al. | |
| 2001/0000795 A1 | 5/2001 | Bolian, II et al. | |
| 2001/0003148 A1 | 6/2001 | Coffee | |
| 2002/0062097 A1* | 5/2002 | Simpson | 602/46 |
| 2002/0133502 A1 | 9/2002 | Rosenthal et al. | |
| 2003/0050794 A1 | 3/2003 | Keck | |
| 2003/0233101 A1 | 12/2003 | Lubock et al. | |
| 2004/0015115 A1 | 1/2004 | Sinyagin | |
| 2004/0059199 A1 | 3/2004 | Thomas et al. | |
| 2004/0133143 A1 | 7/2004 | Burton et al. | |
| 2004/0167456 A1 | 8/2004 | Kingsford et al. | |
| 2005/0149259 A1 | 7/2005 | Cherveny et al. | |
| 2006/0020235 A1 | 1/2006 | Siniaguine | |
| 2006/0034816 A1 | 2/2006 | Davis et al. | |
| 2007/0118096 A1 | 5/2007 | Smith et al. | |
| 2007/0204691 A1 | 9/2007 | Bogner et al. | |
| 2007/0207688 A1 | 9/2007 | Rasor | |
| 2007/0237812 A1 | 10/2007 | Patel et al. | |
| 2008/0004904 A1 | 1/2008 | Tran | |
| 2008/0051688 A1* | 2/2008 | Lowe | 602/58 |
| 2008/0077091 A1 | 3/2008 | Mulligan | |
| 2008/0108923 A1 | 5/2008 | Sinyagin | |
| 2008/0108927 A1 | 5/2008 | Sinyagin | |
| 2008/0234618 A1 | 9/2008 | Baldock | |
| 2009/0024067 A1 | 1/2009 | Siniaguine | |
| 2009/0037224 A1 | 2/2009 | Raduchel | |
| 2009/0131825 A1 | 5/2009 | Burbank et al. | |
| 2009/0204423 A1 | 8/2009 | DeGheest et al. | |
| 2009/0216553 A1 | 8/2009 | Cellura | |
| 2009/0245603 A1 | 10/2009 | Koruga et al. | |
| 2010/0114256 A1 | 5/2010 | Chan et al. | |
| 2010/0219546 A1 | 9/2010 | Puttler et al. | |

FOREIGN PATENT DOCUMENTS

| | | |
|---|---|---|
| WO | WO 97/42917 A1 | 11/1997 |
| WO | WO 00/43046 A2 | 7/2000 |

OTHER PUBLICATIONS

European Search Report, EP 03 72 8787.7, dated May 24, 2006, 4 pages.

Examination Report of the European Patent Office, EP 03 72 8787.7, dated May 18, 2007, 7 pages.

International Search Report, PCT/US03/14574, mailing date Oct. 1, 2003.

PCT International Search Report and Written Opinion, PCT/US2009/048412, Oct. 13, 2009, 13 pages.

PCT International Search Report and Written Opinion, PCT/US2005/25362, Sep. 1, 2006, 9 pages.

Siniaguine, O., "Automatic System for On-Demand Fabrication of Wound Dressings," 2007, pp. 1-15.

United States Office Action, U.S. Appl. No. 10/431,888, Aug. 17, 2009, 17 pages.

United States Office Action, U.S. Appl. No. 10/431,888, Jun. 23, 2009, 14 pages.

United States Office Action, U.S. Appl. No. 10/431,888, Nov. 25, 2008, 11 pages.

United States Office Action, U.S. Appl. No. 10/431,888, Dec. 11, 2007, 8 pages.

United States Office Action, U.S. Appl. No. 10/431,888, Apr. 10, 2007, 7 pages.

United States Office Action, U.S. Appl. No. 11/972,854, Feb. 2, 2010 14 pages.

United States Office Action, U.S. Appl. No. 11/972,854, Jun. 24, 2009, 8 pages.

United States Office Action, U.S. Appl. No. 11/972,846, Jan. 25, 2010, 12 pages.

United States Office Action, U.S. Appl. No. 11/972,846, Jun. 24, 2009, 8 pages.

United States Office Action, U.S. Appl. No. 12/198,604, Jan. 21, 2010, 30 pages.

United States Office Action, U.S. Appl. No. 12/198,604, Jun. 25, 2009, 12 pages.

United States Office Action, U.S. Appl. No. 12/198,676, Sep. 16, 2009, 8 pages.

United States Office Action, U.S. Appl. No. 11/183,459, May 9, 2008, 9 pages.

United States Office Action, U.S. Appl. No. 10/382,422, May 2, 2005, 16 pages.

U.S. Appl. No. 10/431,058.

U.S. Appl. No. 12/164,451, filed Jun. 30, 2008, Siniaguine.

U.S. Appl. No. 12/196,908, filed Aug. 22, 2008, Siniaguine.

U.S. Appl. No. 12/198,604, filed Aug. 26, 2008, Siniaguine.

U.S. Appl. No. 12/198,676, filed Aug. 26, 2008, Siniaguine.

U.S. Appl. No. 11/183,459, filed Jul. 8, 2005, Siniaguine.

U.S. Appl. No. 12/436,071, filed May 5, 2009, Siniaguine.

International Search Report, PCT/US08/50762, mailing date Jun. 25, 2008.

Written Opinion of the International Searching Authority, PCT/US08/50762.

Canadian Examination Report, Canadian Application No. 2,524,934, Feb. 8, 2010, 3 pages.

European Examination Report, European Application No. 03728787.7, Feb. 26, 2010, 4 pages.

International Search Report and Written Opinion, PCT/US2009/054458, Oct. 9, 2009, 3 pages.

United States Office Action, U.S. Appl. No. 12/198,676, Mar. 12, 2010, 7 pages.

U.S. Appl. No. 10/431,888, filed May 7, 2003, Sinyagin.

U.S. Appl. No. 11/972,854, filed Jan. 11, 2008, Sinyagin.

U.S. Appl. No. 11/972,846, filed Jan. 11, 2008, Sinyagin.

U.S. Appl. No. 10/382,422, filed Mar. 5, 2003, Sinyagin.

U.S. Appl. No. 12/110,228, filed Apr. 25, 2008, DeGheest et al.

U.S. Appl. No. 12/436,071, filed May 5, 2009, Siniaguine et al.

PCT International Search Report and Written Opinion, PCT/US2010/031912, Jun. 18, 2010, 13 pages.

International Search Report, PCT/US09/039545, mailing date May 29, 2009.

Written Opinion of the International Searching Authority, PCT/US09/039545.

European Extended Search Report, European Application No. 05773145.7, Jan. 4, 2011, 10 pages.

European Examination Report, European Application No. 03728787.7, Nov. 15, 2010, 6 pages.

United States Office Action, U.S. Appl. No. 12/110,228, Oct. 22, 2010, 21 pages.

United States Office Action, U.S. Appl. No. 12/436,071, Oct. 22, 2010, 18 pages.

United States Office Action, U.S. Appl. No. 12/198,676, Jan. 19, 2011, 8 pages.
United States Office Action, U.S. Appl. No. 10/431,888, Jun. 10, 2010, 18 pages.
"IMPAC Introduces Comprehensive Cancer Outcomes Analytical Suites," Business Wire, published Mar. 7, 2000. Dialog, (File 610 Business Wire), Dialog ID No. 00210331.
"Iteration" Wikipedia, 3 pages, [Online] [Retrieved on Feb. 28, 2011] Retrieved from the Internet<URL:www.wikipedia.com>.
United States Office Action, U.S. Appl. No. 12/110,228, Mar. 7, 2011, 21 pages.
United States Office Action, U.S. Appl. No. 12/436,071, Apr. 1, 2011, 20 pages.
United States Office Action, U.S. Appl. No. 12/198,676, May 13, 2011, 8 pages.
United States Office Action, U.S. Appl. No. 12/110,228, Jul. 28, 2011, 21 pages.
United States Office Action, U.S. Appl. No. 12/436,071, Aug. 24, 2011, 19 pages.
United States Office Action, U.S. Appl. No. 12/198,676, Sep. 6, 2011, 8 pages.
United States Office Action, U.S. Appl. No. 12/164,451, Oct. 13, 2011, 17 pages.
United States Office Action, U.S. Appl. No. 12/196,908, Sep. 30, 2011, 7 pages.
United States Office Action, U.S. Appl. No. 12/110,228, Jan. 31, 2012, 20 pages.
European Examination Report, European Application No. 05773145.7, Jan. 17, 2012, 5 pages.
United States Office Action, U.S. Appl. No. 12/436,071, Feb. 13, 2012, 18 pages.
United States Office Action, U.S. Appl. No. 13/052,553, Mar. 20, 2012, 9 pages.

* cited by examiner

FIG. 7A
FIG. 7B
FIG. 7C
FIG. 7D
FIG. 7E
FIG. 7F
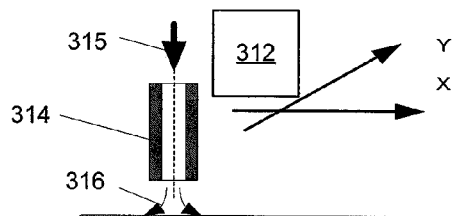
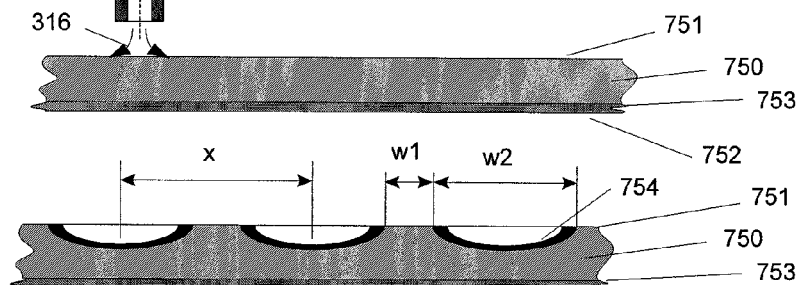
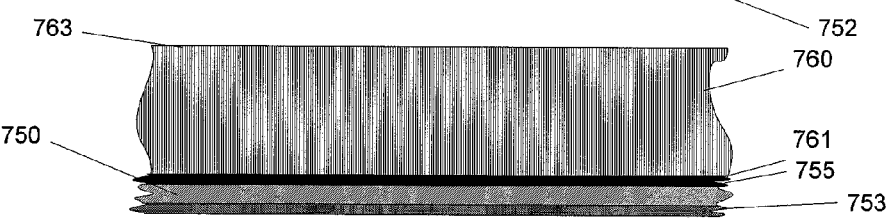
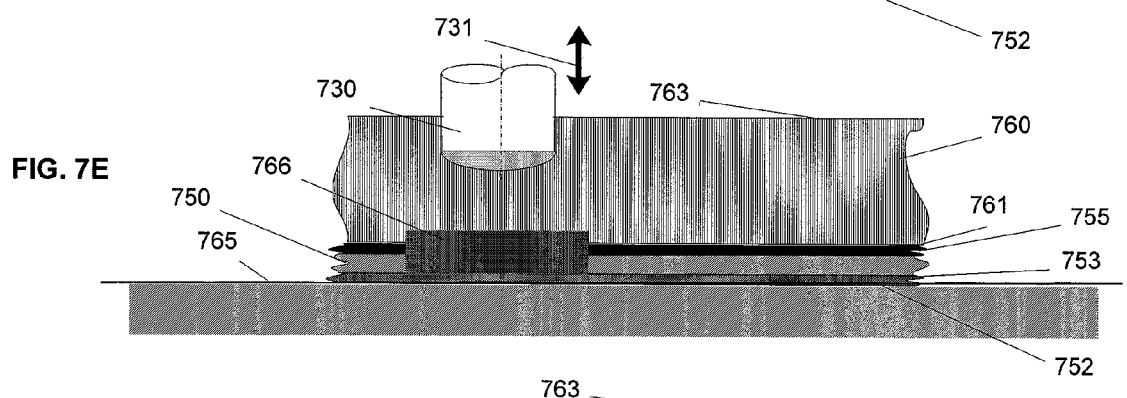
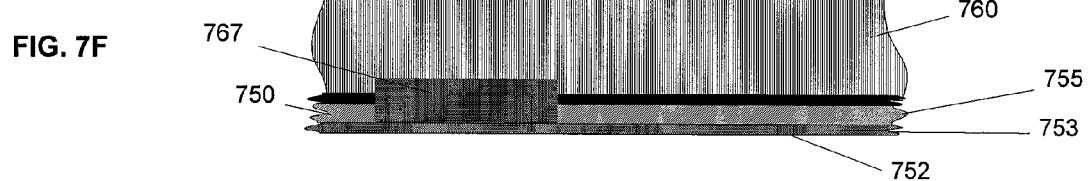

WOUND DRESSING WITH CONTROLLABLE PERMEABILITY

CROSS-REFERENCE TO RELATED APPLICATIONS

This application claims the benefit of U.S. Provisional Application No. 60/884,321, filed Jan. 10, 2007, and U.S. Provisional Application No. 60/888,693, filed Feb. 7, 2007, the disclosures of which are incorporated by reference herein in their entireties.

FIELD OF THE INVENTION

This disclosure of invention relates to wound dressing materials and to methods of manufacture thereof.

BACKGROUND

Currently, the common method of wound treatment is to cover the wound with a wound dressing. The wound dressing is manufactured as a precut sheet of multi-layer material of various shapes and sizes. The wound dressing is applied to cover the wound and a portion of the surrounding healthy skin. Sometimes the wound dressing is cut to reduce the size and to better fit the wound size and shape. This reduces the amount of healthy skin covered by the dressing.

A typical wound commonly has two or more different regions or areas, including necrotic, sloughy, bacteria colonized, granulating, epitheliazing, bleeding, exudating, and drying, which are surrounded by healthy skin tissue. The wound and its various areas are usually of irregular shapes. Consequently, covering the whole wound area and surrounding healthy skin with the same standard dressing type may create adverse conditions for certain areas of the wound or the surrounding skin, which may increase the healing time or even cause adverse effects such as secondary dermatitis.

Basic principles for wound treatment are: (a) keep wound moist, (b) control excessive exudate, (c) keep healthy skin dry. Generally speaking, a wound is a non-homogeneous object. Within the same wound there may be simultaneously exudating and drying tissue areas. So a wound caregiver, if he or she was to recognize the treatment expedients of each unique wound area, would need absorptive and moisturizing properties combined within one dressing. However, to control local properties of the dressing from highly moisture vapor permeable to low moisture vapor permeable on-demand is a challenge.

Therefore, in view of the here recognized idea of treating each wound area uniquely according to its characteristics, it would be desirable to provide a method for wound care that provides the optimal targeted moisture vapor control conditions for wound healing in each wound area by matching the size, shape, and water and water vapor retaining property of each of different areas in a wound dressing to the correspondingly targeted wound areas and current wound conditions. It would also be desirable to provide a system to produce such a wound dressing.

SUMMARY

In accordance with embodiments of the present invention, wound dressings and methods of manufacturing wound dressings are provided. The wound dressings include portions that are converted from a moisture vapor permeable material (non-occlusive) to a material having reduced moisture vapor permeability (semi-occlusive or occlusive). Typical non-occlusive materials have a moisture vapor transmission rate (MVTR)>2 g/sq·cm/24 hour. Typical occlusive materials have an MVTR<0.05 g/sq·cm/24 hour. A semi-occlusive material will have an MVTR in between. The conversion may be accomplished in a variety of ways. In some embodiments, a solvent is used to dissolve a porous material to thereby form a non-porous film. In other embodiments, heat is applied to melt a porous material to thereby form a non-porous film. The heat may be applied using, e.g., a heated gas or a heating element to directly or indirectly heat the material. The conversion of the material using a solvent or heat causes the material to experience a temporary phase change, e.g., from a solid to a liquid and then back to a solid. This temporary phase change can change the form of the material from a fibrous layer to a solid film, thereby modifying the moisture vapor permeability of the material.

In some embodiments, the wound dressings comprises multiple layers. The layer which has portions converted from a water vapor permeable material to a water vapor impermeable material may be provided in various locations among the layers. The converted layer may be provided between two layers which are not converted. In this case, the solvent or heat will pass through a first layer before reaching the converted layer. The first layer comprises a material which is water vapor permeable but does not react to the conversion method to convert into a water vapor impermeable material. For example, the first layer may comprise a material that is not soluble in the solvent used to dissolve the converted layer. In other cases, the first layer may comprise a material which has a higher melting point than the converted layer. The heat that is applied to melt the converted layer passes through the first layer without melting the first layer. The melting of the converted layer in a multi-layer dressing may also be used to bond multiple layers together.

Other features and aspects of the disclosure will become apparent from the following detailed description, taken in conjunction with the accompanying drawings which illustrate, by way of example, the features in accordance with embodiments of the disclosure. The summary is not intended to limit the scope of the disclosure.

DESCRIPTION OF THE DRAWINGS

FIGS. 7A-7F illustrate a method of fabricating a wound dressing with controllable permeability.

DETAILED DESCRIPTION

Figure 1A:
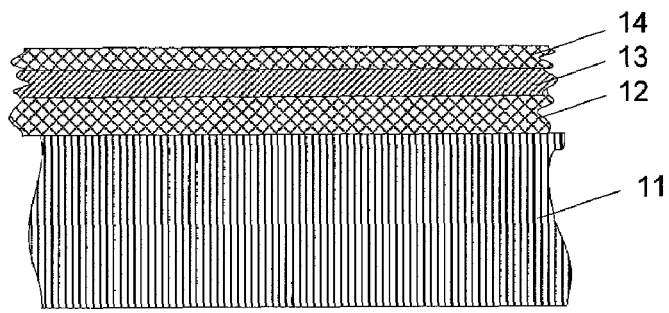
FIGS. 1A-1D are cross-sectional views showing a dressing comprising a material having a sub-surface convertible layer and process steps of forming a barrier film in accordance with embodiments of the present invention.

In the following description, reference is made to the accompanying drawings which illustrate several embodiments of the present disclosure of invention. It is understood that other embodiments may be utilized and changes may be made without departing from the spirit and scope of the present disclosure. The following detailed description is not to be taken in a limiting sense.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present disclosure.

The terminology used herein is for the purpose of describing particular embodiments only and is not intended to be limiting of the invention. Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

As used herein, the singular forms "a", "an" and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

FIGS. 1A-1D show a dressing 10 comprising a material having a sub-surface convertible layer and process steps of forming a barrier film in accordance with embodiments of the present invention.

In this embodiment, the dressing 10 comprises four layers 11-14. When the dressing 10 is applied to a patient, the layer 11 would be facing the patient's wound. The layer 11 may comprise a hydrophilic and highly absorptive, non-woven, fiber-based material or foam. The material may comprise a polymer microfiber and/or a polymer nanofiber. Microfibers are fibers with strands of less than one denier and may comprise polyamides, polyvinyl alcohol, cellulose or polyurethane and blends thereof. Nanofibers are fibers with diameters less than 100 nanometers (nm). The thickness of the layer 11 may be, e.g., 1 mm. In other embodiments, the thicknesses of the various layers of the dressing 10 may vary.

The layer 12 serves as a bulk water and bacteria barrier for the dressing. The layer 12 may comprise hydrophobic polymer polycaprolactone (PCL), Mw>100,000 (GPC), available from Scientific Polymer Products, Inc., of Ontario, N.Y. PCL is a biocompatible polymer widely used in implantable medical devices. The fiber size is in the range 100-800 nm with an average pore size about 500 nm. The thickness of the layer 12 may be, e.g., 100+/−5 micron. The layer 12 may be made of a film which has a high moisture vapor transmission rate but is substantially liquid and microbe impermeable.

The layer 13 is a convertible layer positioned on top of layer 12. The layer 13 is covered by the top layer 14. The top layer 14 may comprise the same material as layer 12 and may serve as an external layer of the wound dressing.

The convertible layer 13 may comprise a mixture of two fiber types: soluble and non-soluble in a selective solvent. The non-soluble fibers serve as a scaffold between the layers 12 and 14 to provide mechanical integrity when the soluble fibers of the layer 13 are dissolved. The material for the non-soluble fibers may be the same as the material forming layers 12 and 14, e.g., PCL.

PCL is known to be soluble in acetone, ethyl acetate, and chloroform but not soluble in alcohols. Isopropanol may be used as a selective solvent for the soluble fibers of the layer 13. One suitable solvent is poly(n-butil methacrylate) (PBMA), Mw>100,000 (GPC), available from Scientific Polymer Products, Inc., of Ontario, N.Y. PBMA is known as a biocompatible polymer and is approved by FDA for use in implantable medical devices.

In some embodiments, the fiber size of the layer 13 may be in the range of 1-5 microns with an average pore size about 3 microns. Layer 13 may be provided with a different fiber size and pore size from layers 12 and 14 to facilitate easier visual recognition of the layers. In other embodiments, the fiber size and pore size of the various layers may be similar or identical.

FIGS. 1A-1D illustrate a method of manufacturing the dressing 10 by converting a sub-surface microfiber layer into a barrier film.

In FIG. 1A, the four layers 11-14 are positioned adjacent each other. In some cases, an adhesive is used to couple adjacent layers together prior to conversion of the convertible layer. In other embodiments, the layers 11-14 may be secured together during subsequent process steps by laminating or due to cohesive forces.

Figure 1B:
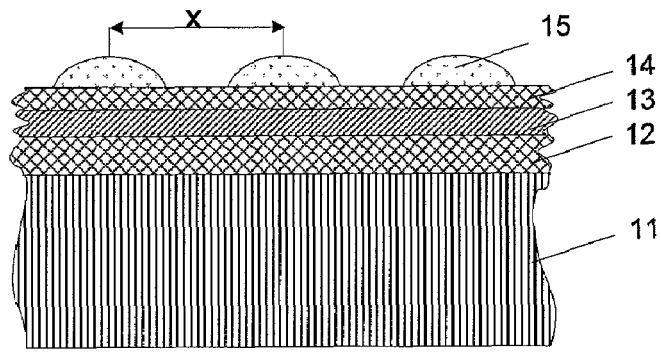
Figure 1C:
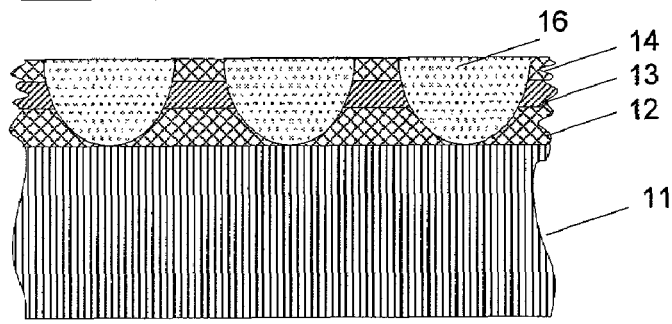

In FIG. 1B, a non-polar solvent 15 is applied to the outer surface of layer 14. The solvent 15 may be applied in a variety of ways. In one example, the solvent 15 is dispensed from a capillary which is translated across the surface of the layer 14, e.g., in the y-direction perpendicular to the page plane of FIG. 1B, at a constant velocity $V_y$. The capillary may also be incrementally moved in the x-direction parallel to the page plane of FIG. 1B. The solvent flow rate and velocity $V_y$ define the amount of solvent dispensed per length unit and the corresponding width of every line as the solvent is absorbed into region 16 of the dressing (shown in FIG. 1C). The estimated optimal volume of the solvent per length unit may be approximately calculated based on the thicknesses of layers 12-14, capillary diameter, and porosity of the material.

Figure 1D:
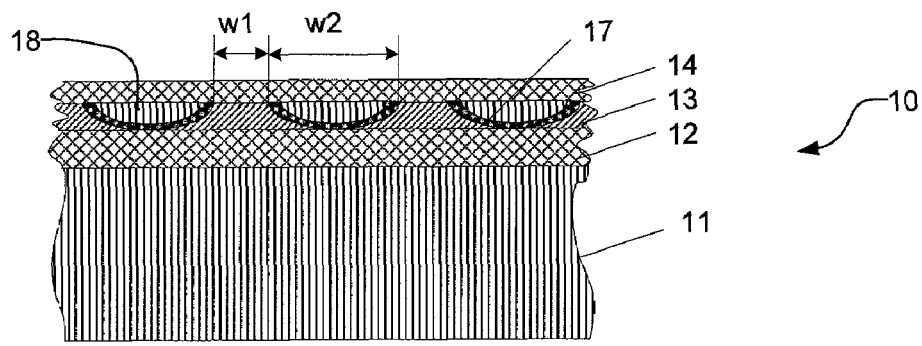

The solvent 15 and materials for layers 12-14 are selected such that the solvent 15 dissolves only the soluble fibers of the layer 13. The portions of layer 13 which are dissolved by the solvent 15 form a water vapor impermeable film 17. The solvent is allowed to evaporate, leaving layers 12 and 14 unaffected, while leaving a pattern of film 17 in layer 13, as shown in FIG. 1D. The undissolved scaffold fibers 18 remain in the region 16 and may be sufficiently stiff to resist solvent surface tension, as shown in FIG. 1D.

Each line of film 17 has a width W2 and may be separated from adjacent film lines by a distance W1. In some embodiments, the width W2 and the separation distances W1 may be varied within a single dressing to thereby provide a controllable size and shape for the impermeable regions of the dressing 10. The values W2 and W1 may be measured by observing a non-woven material cross-section using an optical microscope or scanning electron microscope (SEM). These measurements may be used to adjust the X increment and to vary the ratio of the barrier film area to the total sample area. The SEM observations allow characterizing the resulting conditions of the solidified PBMA film, PCL fiber scaffold, and layers 12 and 13.

The thickness of the film 17 is expected to be a proportional function of the layer 13 thickness and the ratio of soluble/insoluble fibers in that layer. The moisture vapor transmission rate (MVTR) property of the barrier film 17 is a function of its thickness. The overall MVTR may be studied as a function of measured barrier film thickness and ratio W1/W2, and also as a function of the process parameters such as thicknesses of the layer 13 and increment X.

Figure 2A:
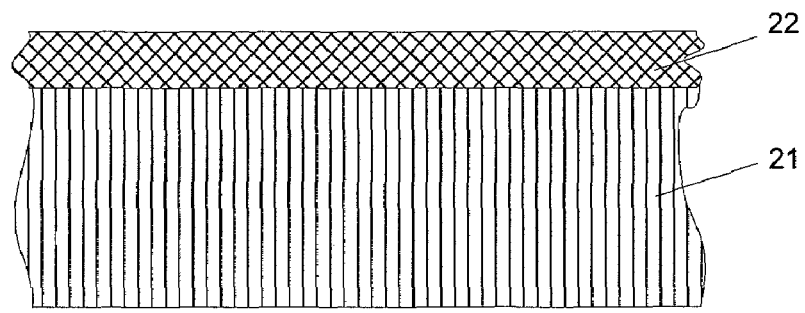
FIGS. 2A-2C are cross-sectional views showing a non-woven material for barrier film casting from a polymer solution and process steps of forming a dressing having this film.
Figure 2B:
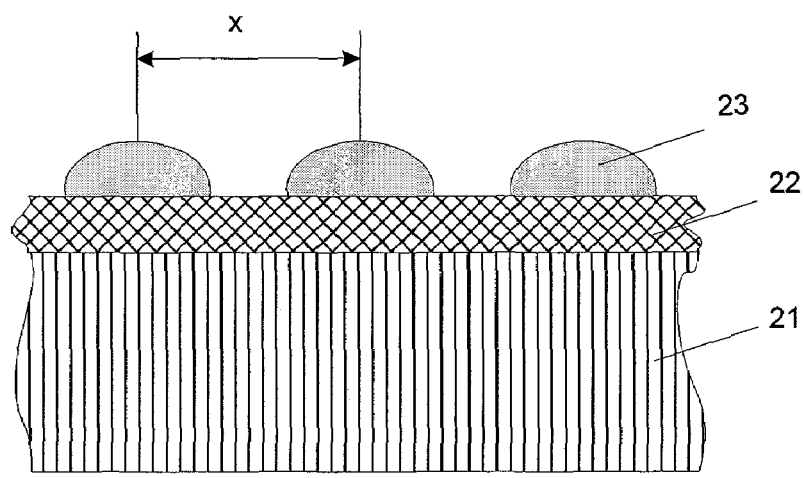
Figure 2C:
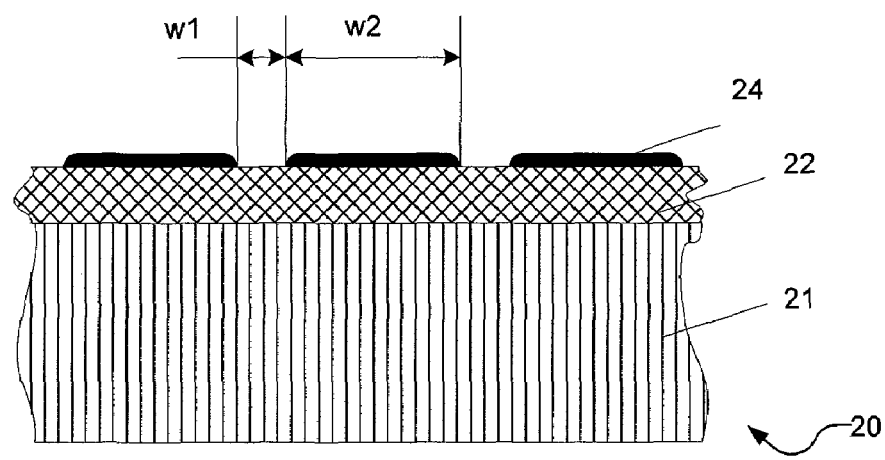

FIGS. 2A-2C illustrate a non-woven material for barrier film casting from a polymer solution and process steps of forming a dressing 20 having this film, in accordance with embodiments of the present invention.

FIG. 2A shows dressing 20 having two layers 21-22, similar to layers 11-12 of FIG. 1A. In FIG. 2B, a polymer solution 23 is applied to the exterior surface of layer 22. The polymer solution 23 may be applied in a variety of ways. In one example, the polymer solution 23 is dispensed from a capillary which is translated across the surface of the layer 22, e.g., in the y-direction perpendicular to the page plane of FIG. 2B, at a constant velocity $V_y$. The capillary may also be incrementally moved in the x-direction parallel to the page plane of FIG. 2B. The solution flow rate and velocity $V_y$ define the amount of solution dispensed per length unit.

The polymer solution is dried to form a barrier film 24 on the exterior surface of the layer 12, as shown in FIG. 2C. The width W2 of every line and the thickness of the film 24 is defined by the polymer solution amount per length unit, polymer concentration in the solution, viscosity and surface tension of the solution, wettability and chemical interaction of the solvent with the layer 12 material (PCL). To minimize the number of process parameters, a 15% solution of PBMA in isopropanol is used for film casting as isopropanol does not dissolve PCL. This concentration may provide a low viscosity solution that is easily dispensed through a capillary and less susceptible to clogging.

The thickness of the film 24 and the distances W2 and W1 may be measured by inspecting a cross-section of the dressing 20 using an optical microscope or scanning electron microscope (SEM). These measurements may be used to adjust the increment X to vary the ratio of the barrier film area to the total sample area.

Figure 3A:
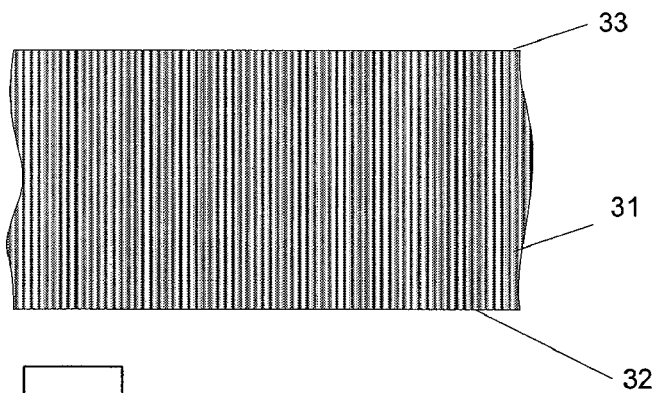
FIGS. 3A-3C illustrate wound dressings 30a, 30b, and a method of fabricating the wound dressing using heat.
Figure 3A:
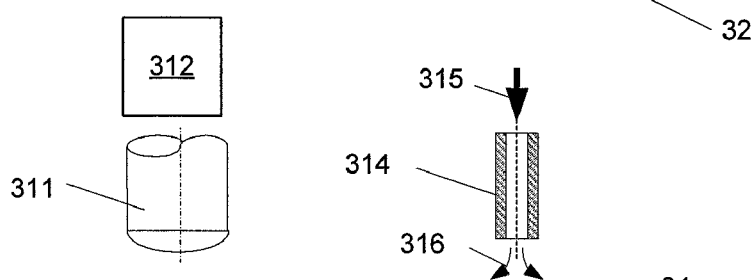
Figure 3B:
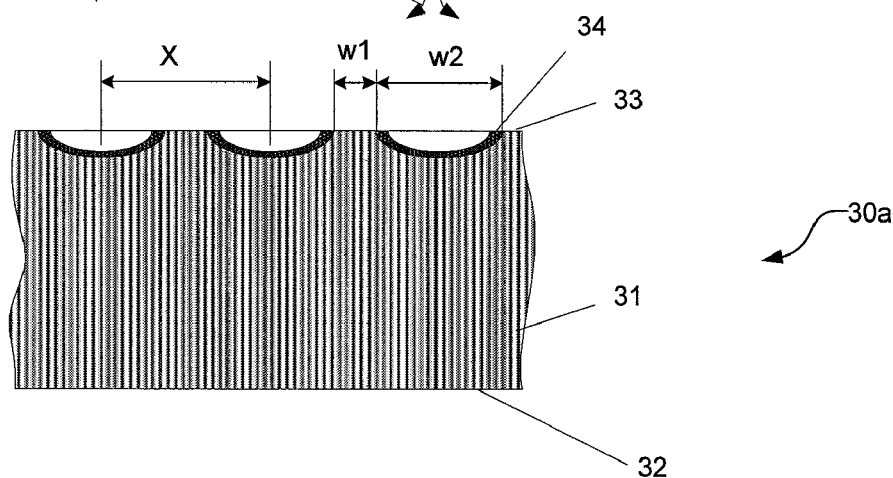
Figure 3C:
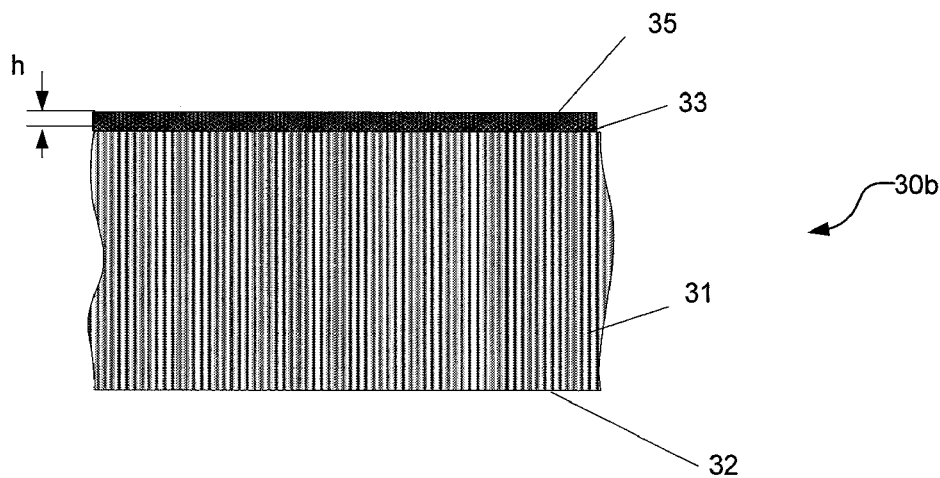

FIGS. 3A-3C illustrate wound dressings 30a, 30b, and a method of fabricating the wound dressing using heat in accordance with embodiments of the present invention. In FIG. 3A, a first layer 31 comprising a microporous or microfiber sheet is provided. A microporous sheet is made of a solid material having pores provided therein. A microfiber sheet is made of separate fibers that are woven or otherwise retained together in sheet form. The first layer 31 has first and second sides 32 and 33. The first side 32 is a wound-facing side and the second side 33 is used for controllable change of the moisture vapor permeability of the dressing 30a or 30b. In one embodiment, the first layer 31 comprises a thermoplastic polymer, e.g., polycaprolactone or nylon.

In FIG. 3B, heat is applied to the second side 33 to convert the material on the second side 33 so as to modify the moisture vapor permeability of the dressing 30a. A heating tool may be positioned in close proximity to the second side 33 and moved along the side 33 with controllable speed and trajectory.

In one embodiment, the heating tool comprises a heating element, such as a metal rod 311. The heating element 311 is heated to a temperature higher than the melting point of the material forming the first layer 31. The heating element 311 may be positioned at a distance 0.1-20 mm from the tip of the heating element 311 to the surface of the side 33 to maximize the heat transfer while avoiding touching and dragging of the melted polymer by the heating element 311. The heating element 311 may be moved by actuators 312 in directions X and Y parallel to the surface of side 33 surface with a programmed velocity $V_y$. The heating element 311 may comprise a gold plated copper rod heated by a barrel type ceramic heater. A thermocouple may provide feedback to a proportional-integral-derivative (PID) temperature controller. The operating temperature may be set at 130+/−2° C. for polycaprolactone and 230° C. for nylon. The heating element may be advanced towards the side 33 in a direction substantially perpendicular to the surface of the side 33.

The heating element 311 heats the surface of the second side 33 to the melting temperature of the polymer. As a result, the porous or microfiber structure of the material on the surface of the second side 33 is converted to a non-porous film 34.

In another embodiment the heating tool may be a nozzle 314 that directs heated gas 315 onto the surface of the second side 33 in a direction substantially perpendicular to the surface of the second side 33. The distance between the outlet of the nozzle 314 and surface of the second side 33 may be, e.g., 1-10 mm, the nozzle diameter may be in the range of 0.5-10 mm, and the flow rate of the heated gas may be 0.1-20 liter/minute. The hot gas temperature is higher than the melting temperature of the material.

The heated gas 315 from the moving nozzle 314 melts the material on the surface of the second side 33, leaving a barrier film 34 in a linear pattern having a line width W2. Non-melted material W1 may remain between the subsequent passes of the heating tool if the incremental shift of the heating toll is larger than the film 34 width W2. This produces a dressing 30a with surface regions having different moisture vapor permeabilities, as shown in FIG. 3B. If the increment X is less than the width W2 then a dressing 30b having a continuous barrier film 35 formed on the second side 33 is produced, as shown in FIG. 3C.

The moisture vapor permeability of the resulting dressing 30b is a function of barrier film thickness h and ratio W1/W2, and also as a function of the process parameters such as thickness of the layer 33 and increment X. The moisture vapor permeability is decreased as the thickness and surface area of the film 34 is increased.

Figure 4A:
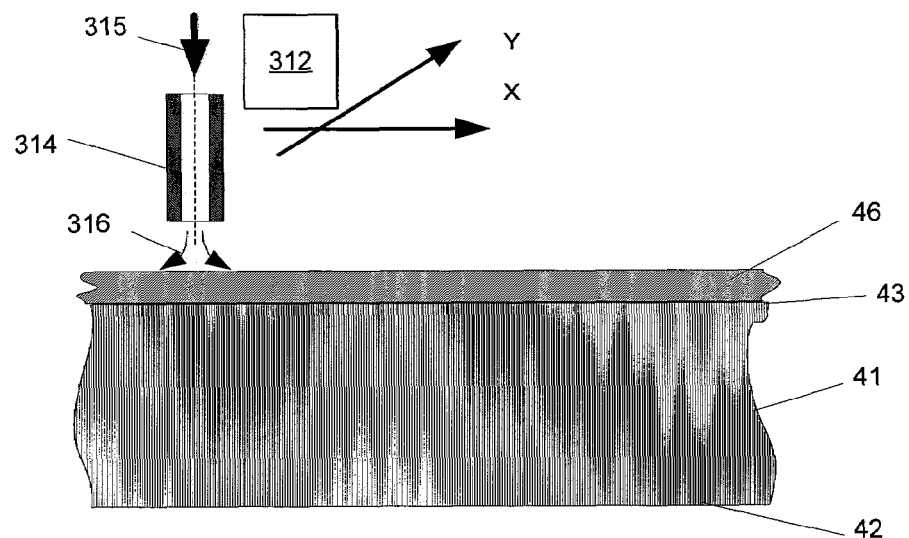
FIGS. 4A-4C illustrate another embodiment in which an auxiliary layer is positioned adjacent to the second side of the first layer.
Figure 4B:
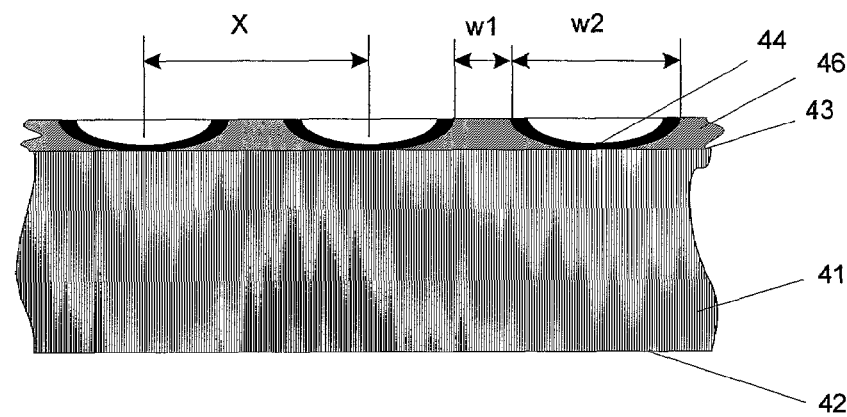
Figure 4C:
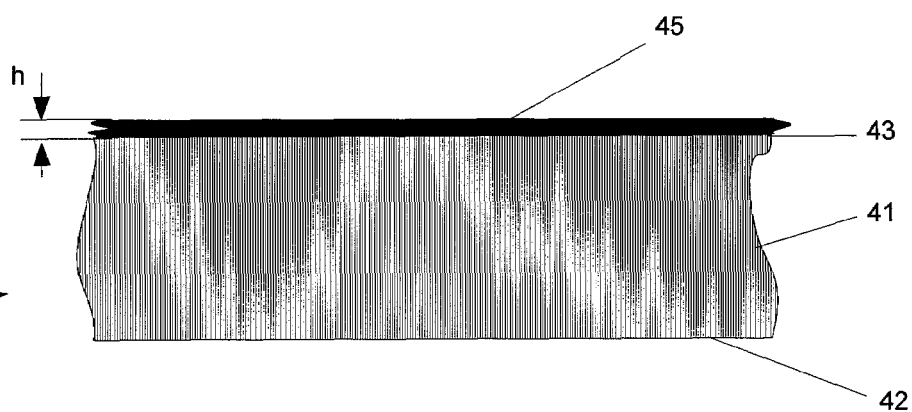

FIGS. 4A-4C illustrate another embodiment in which an auxiliary layer 46 is positioned adjacent to the second side 43 of the first layer 41. The auxiliary layer 46 may comprise a porous material having a high moisture vapor permeability but a lower melting point than the material forming the first layer 41. The first layer 41 may comprise a non-thermoplastic or non-meltable material such as cotton or cellulose. The thickness of the auxiliary layer 46 thickness may be, e.g., 0.1-5 mm. The converted portions of the auxiliary layer 46 may include only portions of the surface of the auxiliary layer 46, thereby producing dressing 40a shown in FIG. 4B, or the converted portions of the auxiliary layer 46 may the entire surface of the auxiliary layer 46, thereby producing dressing 40b shown in FIG. 4C.

In the embodiments illustrated in FIGS. 4A-4C, the first layer 41 serves as a stop layer for the melting of the material of the auxiliary layer 46 during heating by a heating tool 314. As a result the thickness h of the barrier film 44 or 45 is more uniform and less dependable on variations of positioning, temperature and movement of the heating tool 314.

Figure 5A:
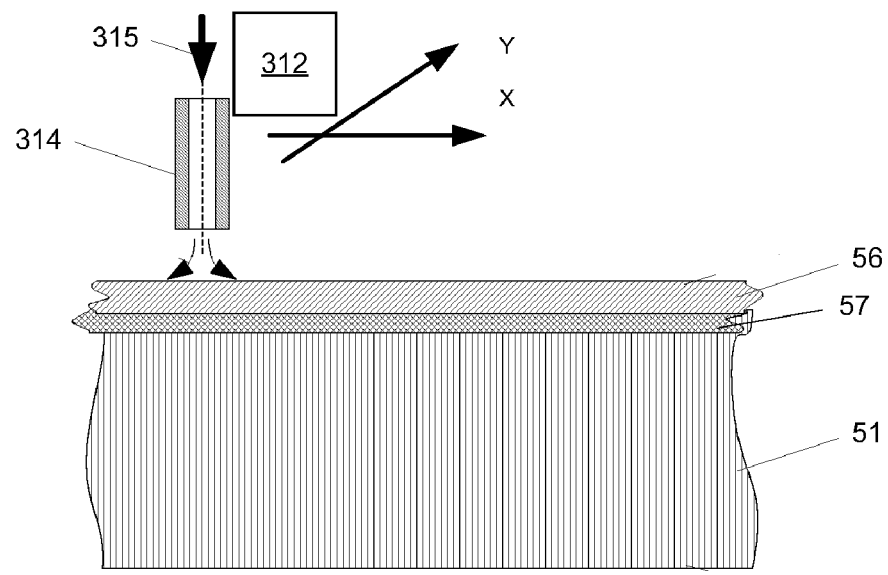
FIGS. 5A-5C illustrate another embodiment in which an additional barrier layer is positioned between the first layer and auxiliary layer.
Figure 5B:
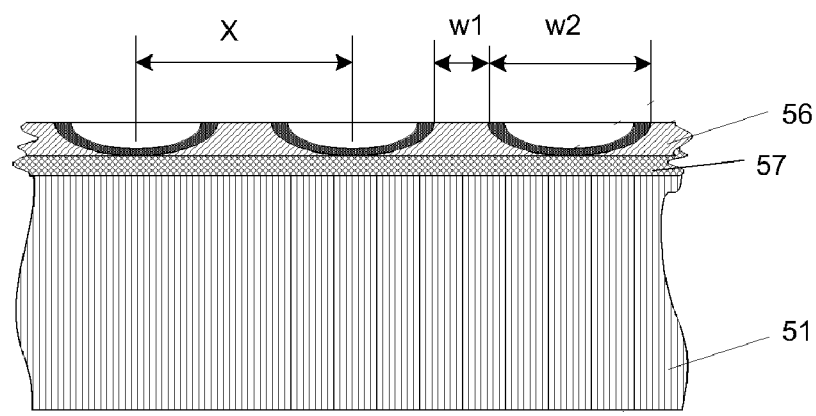
Figure 5C:
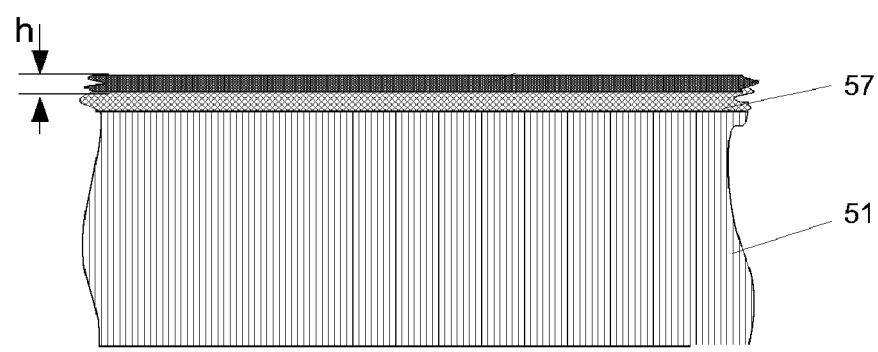

FIGS. 5A-5C illustrate another embodiment in which an additional wicking layer 57 is positioned between the first layer 51 and auxiliary layer 56. The wicking layer 57 has higher melting point than the material forming the auxiliary layer 56 or is non-meltable. The material of the wicking layer 57 may be layer having a moisture vapor permeability greater than, equal to, or less than the first layer 51. The wicking layer 57 serves as a wicking barrier for the melted material of the auxiliary layer 56 to prevent wicking of the melted material into the first layer 51.

Figure 6A:
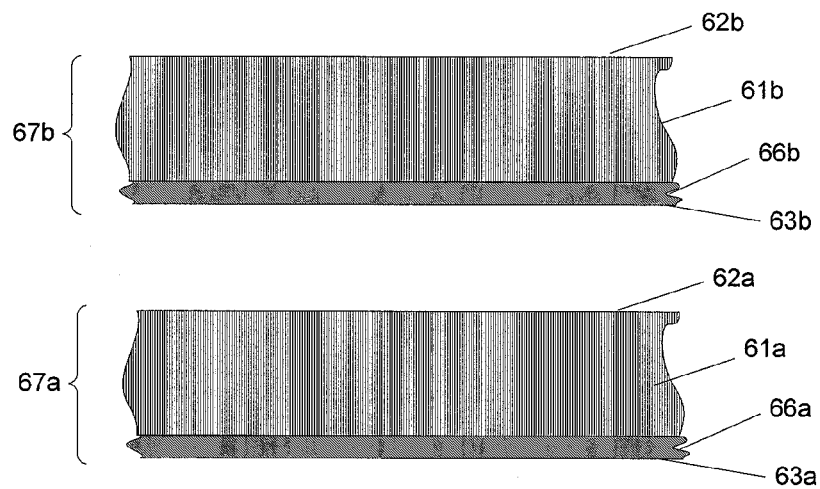
FIGS. 6A-6C illustrate a method of fabricating a dressing having multiple sheets bonded together in stack.
Figure 6B:
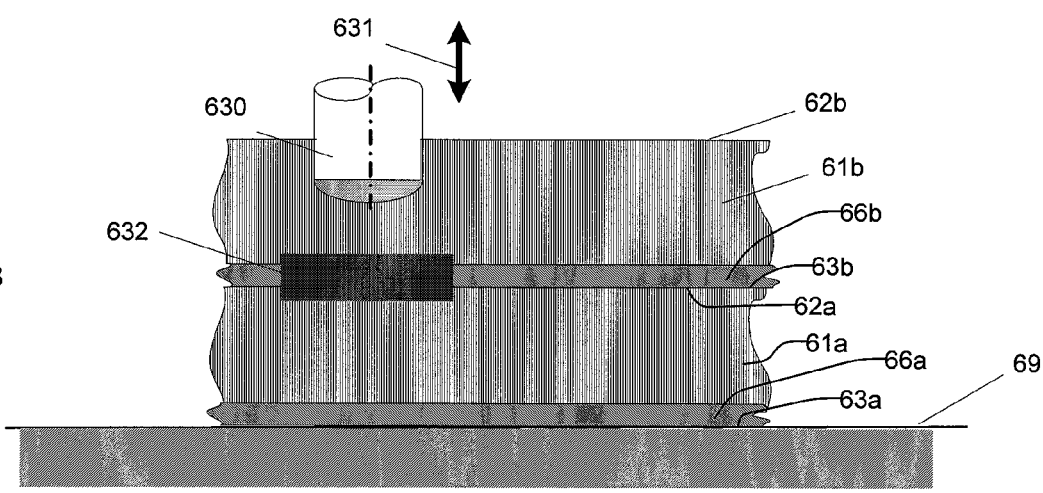
Figure 6C:
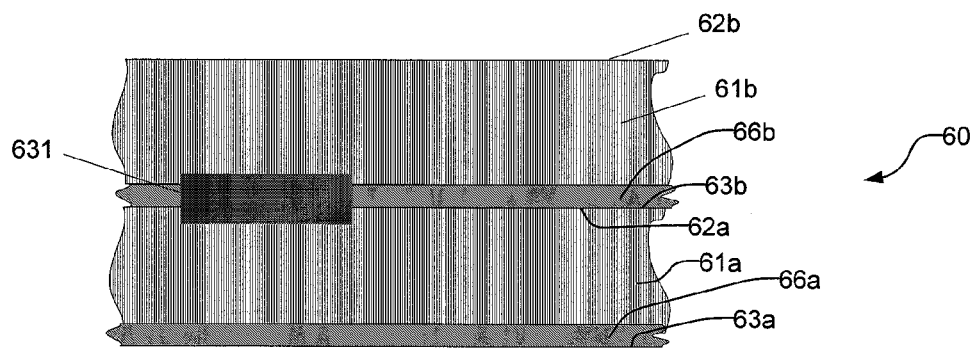

FIGS. 6A-6C illustrate a method of fabricating a dressing 60 having multiple sheets 67a-67b bonded together in stack. The multiple sheets 67 may be bonded without affecting the overall moisture vapor permeability of the resulting multisheet assembly 60. Each sheet 67 comprises a first layer 61 and an auxiliary layer 66, and has a first side 62 and a second side 63. The sheets 67 may be oriented so that the first side 62a of a first sheet 67a faces the second side 63b of an adjacent sheet 67b, as shown in FIG. 6A. In some embodiments, the auxiliary layer 66 of the bottom sheet (sheet 67a in FIG. 6C) may be omitted.

After the sheets 67a-67b are stacked, heat is applied to the stack to melt the auxiliary layer 66b between layer 61a and layer 61b. The melted portions of the auxiliary layer 66b bond the layers 61a-61b together. If the size of the melted portions is small, the overall moisture vapor permeability of the dressing 60 is not significantly impacted, which may be desirable in some cases. In other cases, it may be desirable to reduce the moisture vapor permeability of the dressing 60, in which case a suitable size of the melted portions is chosen to provide the desired permeability.

The auxiliary layer 66b may be melted in a variety of ways. In the embodiment illustrated in FIG. 6B, the stack of sheet 67a-67b is placed on a support 69 and a heating tool 630 is pressed onto the first side 62b of the second sheet 67b. The heating tool is heated to a temperature higher than the melting temperature of the material of the auxiliary layer 66b, but less than the melting temperature of the material forming layers 61a-61b. The heating tool 630 may be, e.g., an aluminum or plated copper rod provided with an actuator 631 to enable the tool 630 to apply a force in direction perpendicular to the support 69. The diameter of the tool 630 may be, e.g., 1-20 mm.

The heat from the heating tool 630 melts the material in the auxiliary layer 66b. Because the stack of sheets 67a-67b is compressed by the tool 630, as shown in FIG. 6B, the molten material from the auxiliary layer 66b permeates portions of the adjacent layers 61a-61b, causing fibers from the layers 61a-61b on either side of the auxiliary layer 66b to be embedded into the molten region 632.

After the heating tool 630 is removed (as shown in FIG. 6C), the molten portion of the auxiliary layer 66b solidifies with the fibers from the layers 61a-61b embedded within, thereby bonding the sheets 67a-67b at the bonding spot 631. Because of the material of the layers 61a-61b is not melted, the properties of the layers 61a-61b in the vicinity of the bonding spot 631 is not affected.

FIGS. 7A-7F illustrate a method of fabricating a wound dressing with controllable permeability in accordance with another embodiment.

In FIG. 7A, a first sheet 752 comprising a support layer 753 and auxiliary layer 750 is provided. In some embodiments, the first sheet 752 may comprise multiple support layers 753 and auxiliary layers 750. The support layer 753 and auxiliary layer 750 are moisture vapor permeable and may comprise microporous or microfiber materials. In some embodiments, the materials are at least partially hydrophobic. The material forming the auxiliary layer 750 has a lower melting temperature than the material forming the support layer 753. The first sheet 752 serves as a bulk water and bacteria barrier for the dressing. The auxiliary layer 750 may comprise hydrophobic polymer polycaprolactone (PCL), Mw>100,000 (GPC). The fiber size may be in the range 100 nm-10 micron. The thickness of the layer 751 may be 10-1000 micron. The support layer 753 may comprise a microporous polyurethane film having a thickness of 1-100 micron.

A heating tool 314 may be used to directed heated gas 315 onto the exterior surface 751 of the auxiliary layer 750. As a result, a portion of the auxiliary layer 750 is melted to form a partial barrier film 754, as shown in FIG. 7B, or a continuous barrier film 755, as shown in FIG. 7C. The temperature of heated gas 315 from the heating tool 314 is higher than melting temperature of the material forming the auxiliary layer 750 but lower than the melting temperature of the material forming the support layer 753. The parameters of heating tool movement, such as linear velocity, spacing X between the consecutive passes, and the thickness of the resulting barrier film 754 or 755 may be determined experimentally to achieve the desired reduction of overall moisture vapor permeability of the dressing.

Next, a sheet 760 comprising a hydrophilic material is positioned adjacent to the sheet 752 such that the sheet 760 faces the barrier film 755 and auxiliary layer 750, as shown in FIG. 7D. The stack of sheets 752 and 760 is placed on a support 765, as shown in FIG. 7E. A heating element 730 is heated to a temperature higher than the melting temperature of the material of the auxiliary layer 750, but less than the melting temperature of the material forming the sheet 760. The heating element 730 may comprise an aluminum or plated copper rod provided with an actuator 731 to move in direction perpendicular to the support 65 plane.

When the sheet stack is compressed by the heated heating element 730, the material in the auxiliary layer 750 and in the previously melted barrier film 755 is melted and permeates portions of the sheet 760, causing fibers from the sheet 760 to be embedded into the molten region 766.

After the heating element 730 is removed (as shown in FIG. 7F), the molten portion of the auxiliary layer 750 solidifies with the fibers from the sheet 760 embedded within, thereby bonding the sheet 760 with sheet 752 at the bonding spot 767. If the layer 753 is made of a liquid impermeable film, then the molten material does not permeate it. If the layer 753 is made of a liquid permeable film, then the molten material may also permeate portions of the layer 753. Because the material forming the sheet 760 is not melted, the properties of the sheet 760 in the vicinity of the bonding spot 766 is not affected. The overall permeability of the wound dressing is defined by the permeability of the barrier film 754 or 755 of the sheet 752. The surface 763 of the sheet 760 is used for contacting a wound when the dressing is applied.

Figure 8A:
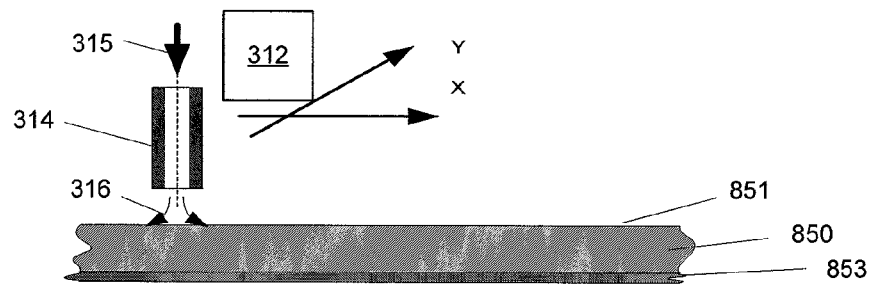
FIGS. 8A-8F illustrate another method of fabricating a wound dressing with controllable permeability.
Figure 8B:
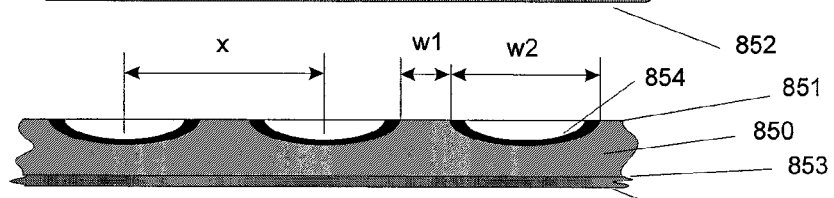
Figure 8C:
Figure 8D:
Figure 8E:
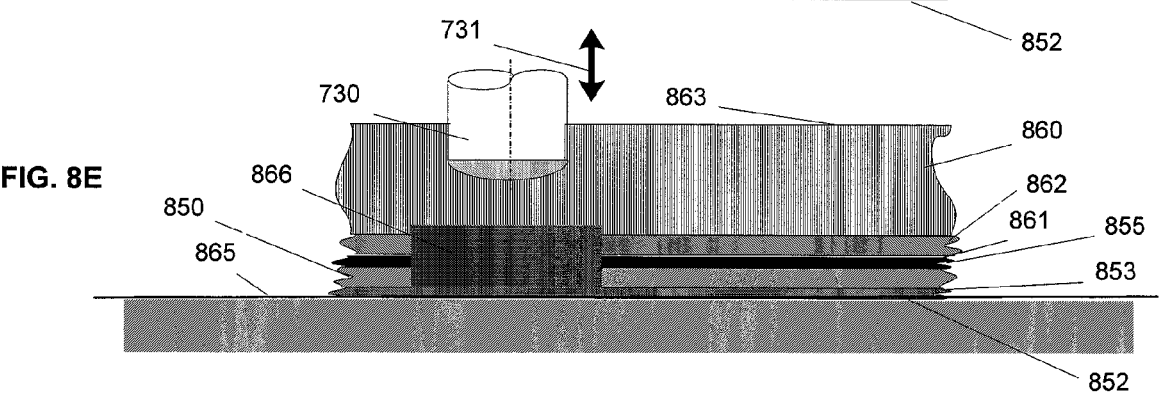
Figure 8F:
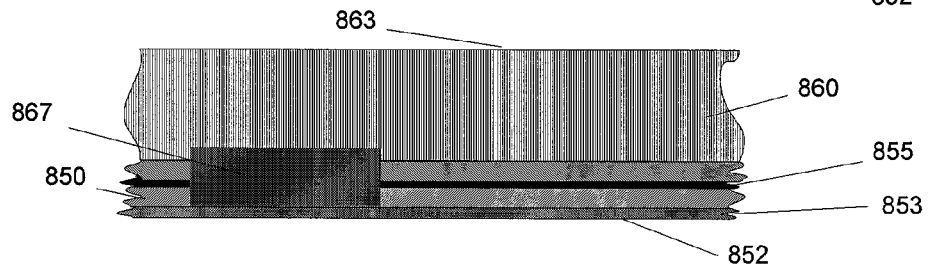

FIGS. 8A-8F illustrate another embodiment similar to the embodiment illustrated in FIGS. 7A-7F, except that the sheet 860 is provided with and additional auxiliary layer 862, as shown in FIG. 8D. The melting temperature of the additional auxiliary layer 762 is similar to the melting temperature of the auxiliary layer 751. One or more sheets 760 may be positioned on top of the sheet 750 so that the additional auxiliary layer 862 faces the barrier film 755. The method of bonding of the sheets 752 and 860 as shown in FIGS. 8A-8F is similar to method shown in FIGS. 7A-7F, except that when heat is applied by the heating element 730, the additional auxiliary layer 762, the barrier film 754 or 755, and the auxiliary layer 750 are melted to form the molten region 866.

When applying a bandage to a wound, a retaining layer is often applied over the top of the dressing to retain the dressing firmly against the wound surface. This layer could be an adhesive bandage layer or could be a gauze wrapped over the dressing and around a limb. The retaining layer applies a pressure onto the dressing to retain the dressing in place. However, in some cases, the force applied by the retaining layer causes the edge of the dressing to dig into the surface of the skin.

Figure 9:
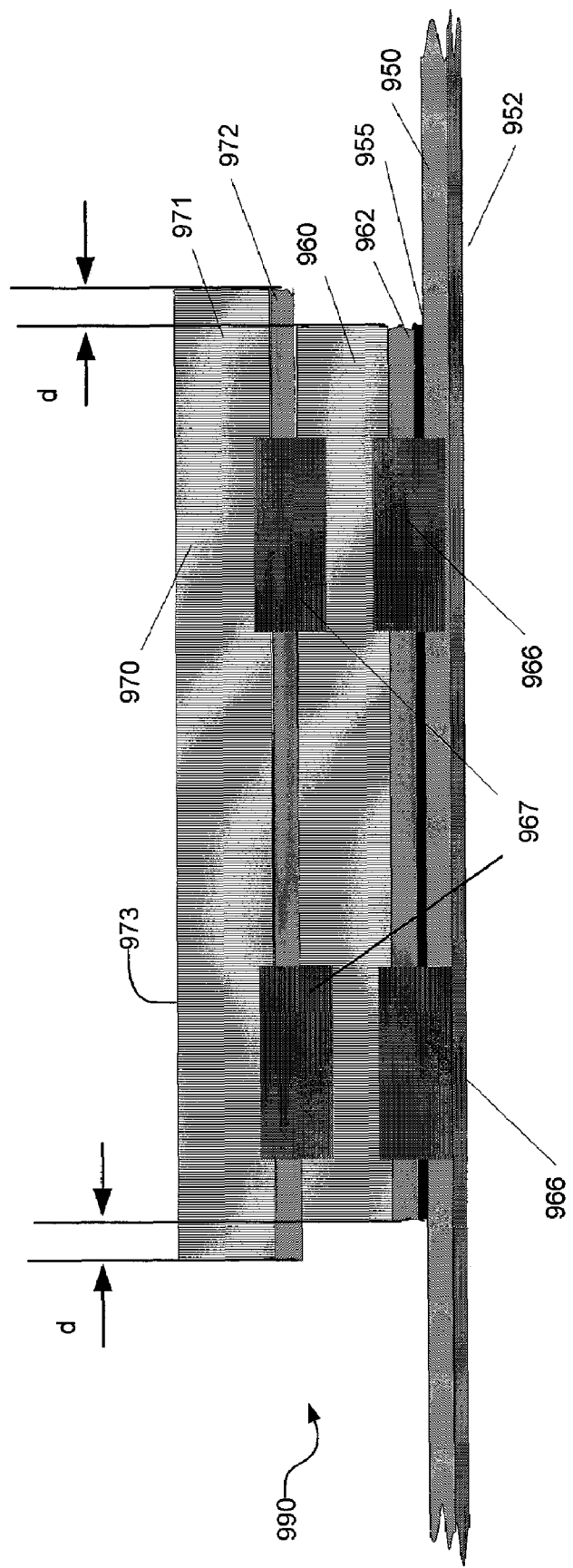
FIG. 9 illustrates another embodiment in which the dressing comprises multiple sheets.

FIG. 9 illustrates another embodiment in which the dressing comprises multiple sheets, with each subsequent sheet having a larger surface area. In the embodiment shown, the edges of the second sheet 970 protrude over the edges of underlying sheet 960 by a distance d that may be, e.g., 0.1 to 10 mm. The resulting dressing 990 has a wound-facing surface 973 on the second sheet 970. The use of multiple sheets having different sizes can reduce the localized pressure on a wound or surrounding skin created by the edge of the dressing 990. The pressure applied by the edge of second sheet 970 on the wound or surrounding skin is reduced because it is not supported by the underlying sheet 960. Thus, the edges of the second sheet 970 can deflect away from the wound or skin without causing excessive pressure.

The materials used to form the various permeable layers described herein may be produced in a variety of ways. Various fiber forming and deposition techniques include electrospinning from a solution, gas blowing from a melt, or any other known technologies. Suitable techniques are described in U.S. Patent Publication No. 2004-0015115 and U.S. Pat. No. 7,105,058, incorporated by reference herein in their entireties.

Examples of suitable polymers to form the microfibers that are at least weakly hydrophobic include such polymers as poly(caprolactone), poly(D,L-lactic acid), polyvinylbutiral, poly (glycolic acid), similar co-polymers of these acids, or any other hydrophobic materials suitable for forming fibers. The microfibers may be colored for matching patient skin color, or other reasons. Other additives or adjuvant may be incorporated into the fibers to enhance an anti-bacterial or anti-viral properties, or to provide odor absorption properties.

Any medical adhesive that is suitable for application to the skin may be optionally applied to the dressing for its attachment to the patient peri-wound skin. The adhesive may be applied with controlled application density per the area unit. The density per the area unit of the applied adhesive can be reduced for lighter strength of the dressing adhesion to the skin, or increased for higher adhesion strength. Any person skillful in the field can easily determine the necessary amount of the adhesive per area unit by a few simple experiments.

In some embodiments, a sterile water or water based solution commonly used for moisturizing wounds, such as saline or a mixture water and glycerin, is applied to the microfiber material through the outer layer of the dressing before application of the dressing to the wound. The amount of the moisturizing agent per area or volume unit of the microfiber material may be controllably varied to achieve the desired moisturizing effect.

The dressing may be cut from a continuous sheet or roll of the microfiber material. The cutting of the dressing may be performing using a tool having a heated tip, with the tip being heated above the melting temperature of the polymers in the microfiber material. A temperature of about 350° C. may be sufficient for cutting the microfiber sheet. The tip of the tool may be cone shaped with an angle of about 45°. With this shape, the cut will be beveled thus reducing potential stress points for the patient skin.

Embodiments of the present invention may provide various advantages not provided by prior art systems. For example, wound dressings may be produced having variable moisture vapor permeability characteristics. In some cases, certain regions within the dressing can have reduced permeability, while other regions maintain a high moisture vapor permeability. In other cases, the overall permeability of the dressing may be adjusted by creating regions of reduced permeability across the entire surface of the dressing. This may be useful in producing wound dressings that are specifically customized to treat a particular patient's wound characteristics.

While the invention has been described in terms of particular embodiments and illustrative figures, those of ordinary skill in the art will recognize that the invention is not limited to the embodiments or figures described. For example, the wound dressing may also comprise additional layers, materials, or additives beyond what is described above. For instance, any of the dressings described herein may be attached to an additional external film for additional strength, aesthetic appearance, or reduced permeability of pressurized water. The film may be made of any polymers or resins and is preferably hydrophobic. The film may provide high water vapor and oxygen permeability greater than 4000 $g/m^2/24$ hour at 37° C. The film material may be chosen so that it is, at least partially, insoluble in the solvent used to convert the permeability of the various layers.

In some embodiments, the surface of the dressing may be made more dense by controlled melting of the micro-fibers forming the outer surface. This may be achieved by positioning a heating element in close proximity to the surface of the dressing and moving the heat element quickly across the surface of the dressing. This rapid heating can be used to melt the fibers on the surface of the dressing without melting the rest of the microfiber layer.

Therefore, it should be understood that the invention can be practiced with modification and alteration within the spirit and scope of the teachings of the present disclosure. The description is not intended to be exhaustive or to limit the invention to the precise form disclosed.

What is claimed is:

1. A wound dressing comprising:
 a first layer having a first region characterized by a respective first moisture vapor transmission rate (MVTR1) and having a second region characterized by a respective second and smaller moisture vapor transmission rate (MVTR2), wherein said first and second regions are shaped and sized to match corresponding regions of the wound;
 a second layer disposed adjacent the first layer, said second layer having a higher melting point than the first layer; and
 a third layer provided above the first layer so that the first layer is sandwiched between the third layer and the second layer, said third layer having a higher melting point than the first layer, where the second and third layers are porous and the third layer has a larger average pore size than that of the second layer.

2. The wound dressing of claim 1, wherein:
 the third layer comprises hydrophobic polymer microfibers.

3. The wound dressing of claim 2, wherein:
the first layer, the second layer, or the third layer includes a substance enhancing wound healing.

4. The wound dressing of claim 2, wherein:
the first layer, the second layer, or the third layer includes a pharmacological substance.

5. The wound dressing of claim 1, wherein:
at least one of the first and second layers comprises hydrophobic polymer microfibers.

6. The wound dressing of claim 1, wherein:
at least one of the first layer and the second layer has bacteriostatic, bactericidal, or antifungal properties.

7. A wound dressing comprising:
a first layer having a first region characterized by a respective first moisture vapor transmission rate (MVTR1) and having a second region characterized by a respective second and smaller moisture vapor transmission rate (MVTR2), wherein said first and second regions are shaped and sized to match corresponding regions of the wound; and
a second layer disposed adjacent the first layer, said second layer having a higher melting point than the first layer, wherein said second layer comprising a material insoluble in the first solvent and the first layer comprises a first microfiber type and a second microfiber type, said first microfiber type being soluble in a first solvent and the second microfiber type being insoluble in the first solvent.

8. The wound dressing of claim 7, wherein:
the second layer comprises hydrophobic polymer microfibers.

9. A dressing for assisting in healing of a wound to skin of a patient where the wound may have different wound attributes in respective one or more regions of the wound, the dressing comprising:
a first sheet, said first sheet having a first layer generally characterized by a respective first moisture vapor transmission rate (MVTR1) greater than 0.05 g/sq·cm/24 hour and having a second layer characterized by a respective melting point that is smaller than that of the first layer; and
a second sheet comprising a third layer and a fourth layer, wherein the third layer generally characterized by a respective second moisture vapor transmission rate (MVTR2) greater than 0.05 g/sq·cm/24 hour and wherein the fourth layer is characterized by a respective melting point that is smaller than that of the third layer;
wherein the second layer of the first sheet is bonded to the third layer of the second sheet by a melted and resolidified portion of the second layer.

10. The dressing of claim 9, wherein:
a portion of the fourth layer of the second sheet is a selectively converted portion which is locally characterized by a respective third moisture vapor transmission rate (MVTR3) that is smaller than the general first moisture vapor transmission rate (MVTR1) of the first sheet.

11. The dressing of claim 9, wherein:
a lateral dimension of the second sheet is larger than a lateral dimension of the first sheet.

12. The dressing of claim 9, wherein:
the first sheet comprises a first layer and a second layer, wherein the second layer of the first sheet has a lower melting point than the first layer of the first sheet and is bonded to the second layer of the second sheet.

13. The dressing of claim 12, further comprising:
a third sheet comprising a first layer and a second layer, wherein the second layer of the third sheet has a lower melting point than the first layer of the third sheet and is bonded to the first layer of the first sheet.

14. The dressing of claim 13, wherein:
a lateral dimension of the third sheet is larger than a lateral dimension of the first sheet.

15. The dressing of claim 13, wherein:
a lateral dimension of the second sheet is larger than a lateral dimension of the first sheet and a lateral dimension of the third sheet.

* * * * *